(12) United States Patent
Timms et al.

(10) Patent No.: US 12,336,928 B2
(45) Date of Patent: Jun. 24, 2025

(54) DEODORIZING COMPOSITIONS, OSTOMY DEVICES, AND USES THEREOF

(71) Applicant: Emory University, Atlanta, GA (US)

(72) Inventors: Cynthia Timms, Atlanta, GA (US); Ronald Bracken, Monroe, GA (US)

(73) Assignee: Emory University, Atlanta, GA (US)

( * ) Notice: Subject to any disclaimer, the term of this patent is extended or adjusted under 35 U.S.C. 154(b) by 1592 days.

(21) Appl. No.: 16/467,921

(22) PCT Filed: Dec. 7, 2017

(86) PCT No.: PCT/US2017/065030
§ 371 (c)(1),
(2) Date: Jun. 7, 2019

(87) PCT Pub. No.: WO2018/106871
PCT Pub. Date: Jun. 14, 2018

(65) Prior Publication Data
US 2019/0365560 A1    Dec. 5, 2019

Related U.S. Application Data

(60) Provisional application No. 62/431,141, filed on Dec. 7, 2016.

(51) Int. Cl.
*A61F 5/441*    (2006.01)
*A61F 5/445*    (2006.01)
(Continued)

(52) U.S. Cl.
CPC ............. *A61F 5/441* (2013.01); *A61F 5/445* (2013.01); *A61L 9/01* (2013.01); *A61L 28/0015* (2013.01); *A61L 28/0049* (2013.01)

(58) Field of Classification Search
CPC . A61F 5/441; A61F 5/445; A61L 9/01; A61L 28/0015; A61L 28/0049
See application file for complete search history.

(56) References Cited

U.S. PATENT DOCUMENTS 3,765,371 A * 10/1973 Fisher .................. A01K 1/0152
119/171
3,861,993 A     1/1975 Guthrie
(Continued)

FOREIGN PATENT DOCUMENTS

CA    2315892         2/2001
CA    2315892 A1 *    2/2001 ............... A61L 9/01
(Continued)

OTHER PUBLICATIONS

International Search Report and Written Opinion issued for Application No. PCT/US2017/065030, dated Feb. 14, 2018.
(Continued)

*Primary Examiner* — Guy K Townsend
(74) *Attorney, Agent, or Firm* — Meunier Carlin & Curfman LLC

(57) ABSTRACT

This disclosure relates to deodorizing compositions, ostomy devices, and uses thereof. In certain embodiments, the disclosure contemplates a deodorizer comprising a combination of citric acid and a citric acid salt, cocamidopropyl betaine, zinc ricinoleate, and optionally comprising a preservative such as a paraben. In certain embodiments, the deodorizing composition is contained loaded in a hydrogel or hydrophilic polyurethane. In further embodiments, the loaded hydrogel or hydrophilic polyurethane is placed in an ostomy device.

2 Claims, 4 Drawing Sheets

(51) Int. Cl.
*A61L 9/01* (2006.01)
*A61L 28/00* (2006.01)

(56) References Cited

U.S. PATENT DOCUMENTS

| | | | |
|---|---|---|---|
| 3,889,417 A | 6/1975 | Wood et al. | |
| 4,365,025 A | 12/1982 | Murch et al. | |
| 4,384,051 A | 5/1983 | Guthrie | |
| 4,735,935 A | 4/1988 | McAnalley | |
| 5,352,444 A * | 10/1994 | Cox | B09B 3/00 424/617 |
| 5,587,157 A * | 12/1996 | Cox | B09B 3/00 424/688 |
| 5,589,164 A * | 12/1996 | Cox | A61L 9/01 424/688 |
| 5,650,450 A | 7/1997 | Lovette et al. | |
| 5,736,032 A * | 4/1998 | Cox | B09B 3/00 514/699 |
| 6,015,547 A * | 1/2000 | Yam | A61Q 5/02 424/49 |
| 6,034,149 A | 3/2000 | Bleys et al. | |
| 6,129,716 A | 10/2000 | Steer | |
| 6,200,939 B1 | 3/2001 | Maurer | |
| 7,022,746 B2 | 4/2006 | Lockwood et al. | |
| 7,422,577 B2 | 9/2008 | Subraya et al. | |
| 8,557,249 B2 * | 10/2013 | Brooks | A61K 8/922 424/195.17 |
| 8,674,050 B2 | 3/2014 | Spyrou | |
| 9,205,040 B2 * | 12/2015 | Brooks | A61Q 5/02 |
| 9,364,577 B2 | 6/2016 | Niesten | |
| 9,458,300 B2 | 10/2016 | Dorr et al. | |
| 9,597,280 B2 * | 3/2017 | Yaiser | A61K 8/9722 |
| 10,208,241 B2 * | 2/2019 | Agrawal | A61K 8/20 |
| 11,154,474 B2 * | 10/2021 | Monroe | A61L 9/01 |
| 2003/0133892 A1 * | 7/2003 | Lersch | A61K 8/27 424/67 |
| 2005/0058673 A1 * | 3/2005 | Scholz | A61K 9/0046 514/557 |
| 2006/0228323 A1 * | 10/2006 | Novelle | A61L 2/18 424/76.2 |
| 2008/0287538 A1 * | 11/2008 | Scholz | A61P 31/00 514/552 |
| 2009/0148342 A1 * | 6/2009 | Bromberg | C11D 3/124 424/661 |
| 2011/0124573 A1 * | 5/2011 | Gupta | A61K 8/355 514/397 |
| 2013/0028854 A1 * | 1/2013 | Gupta | A61K 8/498 514/23 |
| 2014/0147408 A1 * | 5/2014 | Williams | C11D 3/222 424/76.1 |
| 2014/0257215 A1 * | 9/2014 | Timms | A61L 9/127 604/333 |
| 2014/0271757 A1 * | 9/2014 | Agrawal | C09D 5/14 507/90 |
| 2016/0032180 A1 * | 2/2016 | Agrawal | A61K 8/8176 507/219 |
| 2016/0074294 A1 * | 3/2016 | Monroe | A61K 8/26 424/68 |
| 2016/0135470 A1 * | 5/2016 | Agrawal | A61K 31/555 424/404 |
| 2016/0251571 A1 * | 9/2016 | Agrawal | A61K 8/8152 507/219 |
| 2019/0209450 A1 * | 7/2019 | Monroe | A61Q 15/00 |
| 2019/0365560 A1 * | 12/2019 | Timms | A61L 28/0034 |
| 2022/0160599 A1 * | 5/2022 | Monroe | A61L 9/14 |
| 2022/0313574 A1 * | 10/2022 | Monroe | A61L 9/014 |
| 2024/0382639 A1 * | 11/2024 | Monroe | A61L 9/14 |

FOREIGN PATENT DOCUMENTS

| | | | |
|---|---|---|---|
| DE | 9202862 U1 * | 7/1992 | B65F 7/00 |
| EP | 1749919 | 2/2007 | |
| WO | 2016008517 | 1/2016 | |

OTHER PUBLICATIONS

MINTEL: "Everyday Deodorant", GNPD, MINTEL, Jan. 1, 2010, 3 pages.

European Search Report issued for Application No. EP17878256, dated Jul. 9, 2020.

* cited by examiner

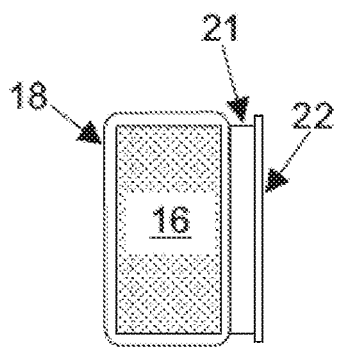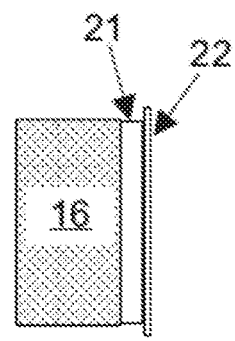
FIG. 2A  FIG. 2B
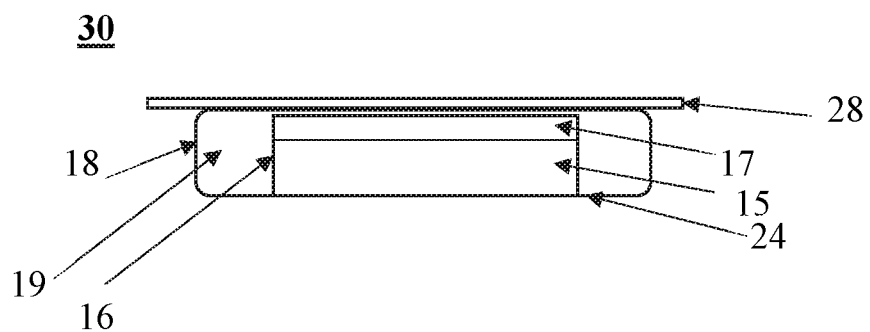
FIG. 2C

DEODORIZING COMPOSITIONS, OSTOMY DEVICES, AND USES THEREOF

CROSS-REFERENCE TO RELATED APPLICATIONS

This application is the National Stage of International Application No. PCT/US2017/065030 filed Dec. 7, 2017, which claims the benefit of U.S. Provisional Application No. 62/431,141 filed Dec. 7, 2016. The entirety of each of these applications is hereby incorporated by reference for all purposes.

BACKGROUND

Surgical creation of an opening (stoma) to allow discharge of biological waste products is often a component in the management of medical conditions such as colorectal cancer, bladder cancer, and inflammatory bowel disease. See Szenwczyk et al. Ostomy Wound Manage. 2014, 60(12):16-26. Ileosotomy, colostomy, and urostomy are surgical procedures in which a stoma is formed by drawing the healthy end of the small or large intestine through the abdominal wall. An attached ostomy pouch provides an alternative channel for excrement. The ostomy pouch can be a plastic bag with a sealable opening used to drain the contents of the pouch. Two-piece system are typically constructed with a mounting plate and a collection pouch. Collection pouches can be removed and replaced, or the pouch can be emptied and rinsed.

Deodorants have been reported to reduce odors in ostomy pouches, and deodorizing compositions for use in ostomy pouches are disclosed in U.S. Pat. Nos. 7,422,577, 6,129,716 and 6,200,939. ConvaTec™ report sachets to be placed directly into the opening of an ostomy pouch. See also Diamonds™ gelling and odor control sachets. Hollister™ sell an ostomy odor eliminator call "m9 Odor Eliminator™." However, there remains a need to identify improved deodorizing methods and compositions.

U.S. Published Patent Application number 2006/0228323 reports compositions for treating and removing noxious materials malodors and microbes.

U.S. Published Patent Application number 2014/0257215 reports containers for holding deodorants.

References cited herein are not an admission of prior art.

SUMMARY

This disclosure relates to deodorizing compositions, ostomy devices, and uses thereof. In certain embodiments, the disclosure contemplates a deodorizer comprising a combination of citric acid and a citric acid salt; cocamidopropyl betaine; zinc ricinoleate; and optionally comprising a preservative such as a paraben. In certain embodiments, the deodorizing composition is contained or loaded in a hydrophilic polyurethane or hydrogel. In further embodiments, the loaded hydrophilic polyurethane or hydrogel is placed in an ostomy device in order to improve the longevity of the deodorizing composition.

In certain embodiments, the disclosure contemplates a deodorizer comprising a) a combination of citric acid and a citric acid salt; b) cocamidopropyl betaine; and c) zinc ricinoleate. In certain embodiments, the deodorizer further comprises tetrahydroxy propyl ethylenediamine; and lauroyl sarcosinate, a lauroyl sarcosinate salt, or combination thereof. In certain embodiments, the deodorizer further comprises a paraben. In certain embodiments, the deodorizer further comprises an antimicrobial agent. In certain embodiments, the antimicrobial agent is diazolidinyl urea. In certain embodiments, the deodorizer further comprises *aloe* derived acetylated polymannose or acemannan.

In certain embodiments, the deodorizer is an aqueous solution and has a total of the combination of citric acid and a citric acid salt in an amount between 5% and 15% by weight or 7% and 9% by weight. In certain embodiments, the deodorizer is an aqueous solution and has cocamidopropyl betaine in an amount between 2% and 10% by weight or 3% and 7% by weight. In certain embodiments, the deodorizer is an aqueous solution and has a total of the zinc ricinoleate, tetrahydroxy propyl ethylenediamine, lauroyl sarcosinate, a lauroyl sarcosinate salt, or combination in an amount between 5% and 15% by weight or 7% and 9% by weight.

In certain embodiments, the disclosure relates to an ostomy device comprising a deodorizer disclosed herein. In certain embodiments, the deodorizer is an aqueous solution and has a total of the combination of citric acid and a citric acid salt in an amount between 35% and 25% or between 30% and 34% by weight. In certain embodiments, the deodorizer is an aqueous solution and has cocamidopropyl betaine in an amount between 14% and 18% by weight. In certain embodiments, the deodorizer is an aqueous solution and has a total of the zinc ricinoleate, tetrahydroxy propyl ethylenediamine, lauroyl sarcosinate, a lauroyl sarcosinate salt, or combination in an amount between 14% and 18% by weight.

In certain embodiments, the disclosure relates to a water absorbent material comprising the deodorizer disclosed herein. In certain embodiments the water absorbent material is a hydrophilic polyurethane or hydrogel.

In certain embodiments, the disclosure relates to the hydrophilic polyurethane comprising water and 35 to 25% by weight a combination of citric acid and citric acid salts, 6 to 3% cocamidopropyl betaine, 4 to 2% zinc ricinoleate, 3 to 1% tetrahydroxy propyl ethylenediamine, and 2 to 0.5% sodium lauroyl sarcosinate.

In certain embodiments, the disclosure relates to a hydrophilic polyurethane comprising water and 25 to 22% by weight citrate salt, 9 to 6% citric acid, 6 to 3% coco betaine, 4 to 2% zinc ricinoleate, 3 to 1% tetrahydroxy propyl ethylenediamine, and 2 to 0.5% sodium lauroyl sarcosinate.

In certain embodiments, the disclosure relates to an ostomy device comprising a water absorbent material disclosed herein.

In certain embodiments, the disclosure relates to a kit comprising a deodorizing composition disclosed herein and a water absorbent material. In certain embodiments, the water absorbent material is a hydrophilic polyurethane or hydrogel. In certain embodiments, the water absorbent material is a hydrophilic polyurethane or hydrogel preloaded with the deodorizing composition. In certain embodiments, the water absorbent material is a hydrophilic polyurethane or hydrogel and the deodorizing composition is in a separate container.

In certain embodiments, the kit further comprising a deodorizing attachment device configured to attach the water absorbent material to the interior of an ostomy device. In certain embodiments, the water absorbent material is at least partially attached to or surrounded by the deodorizing attachment device.

BRIEF DESCRIPTION OF THE DRAWINGS

FIG. 2A illustrate embodiments of a deodorizing device disclosed herein.

FIG. 2B illustrate embodiments of a deodorizing device disclosed herein.

FIG. 2C illustrate embodiments of a deodorizing device disclosed herein.

DETAILED DISCUSSION

Figure 1:
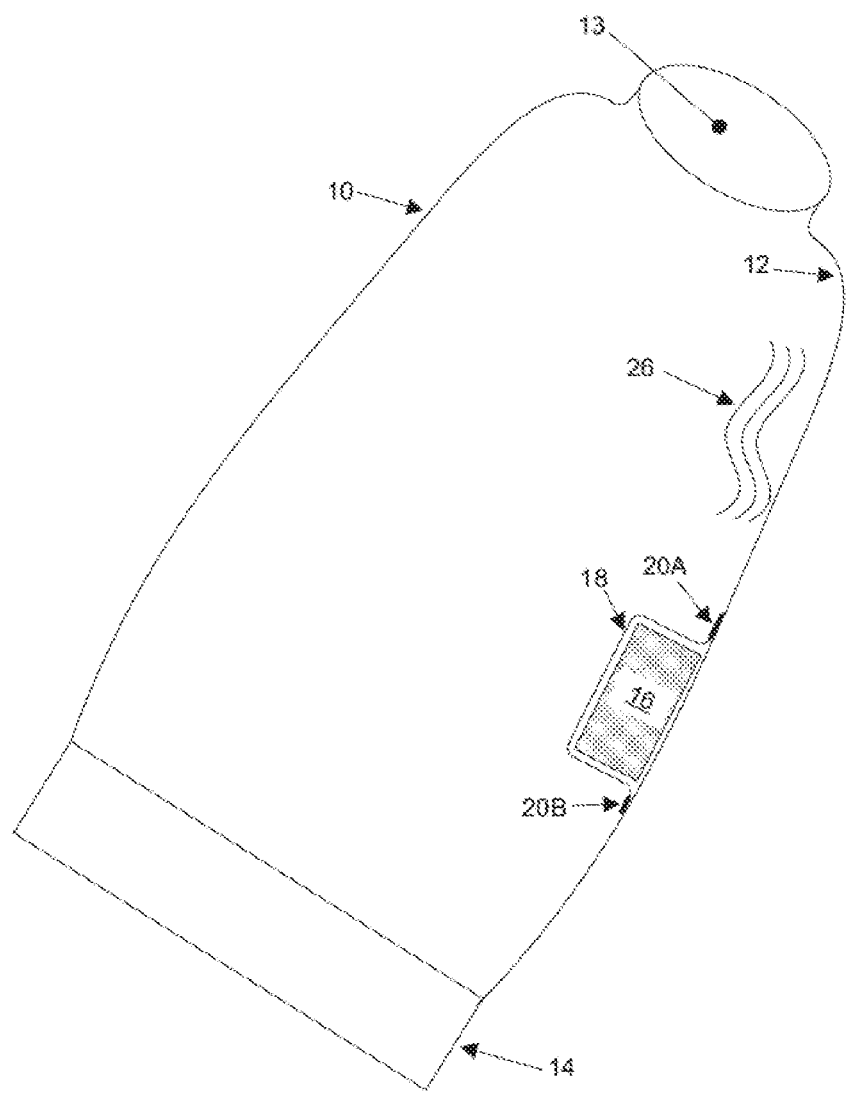
FIG. 1 illustrates an embodiment of an ostomy pouch.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps. "Consisting essentially of" or "consists essentially" or the like, when applied to methods and compositions encompassed by the present disclosure refers to compositions like those disclosed herein that exclude certain prior art elements to provide an inventive feature of a claim, but which may contain additional composition components or method steps, etc., that do not materially affect the basic and novel characteristic(s) of the compositions or methods, compared to those of the corresponding compositions or methods disclosed herein.

The term "coco betanine" or "cocamidopropyl betaine" refers to {[3-(Dodecanoylamino)propyl](dimethyl)ammonio}acetate. It is typically the product of combining chloroacetic acid with the amide of dimethylaminopropylamine and fatty acids from coconut oil. Coconut oil is mainly lauric acid but other acids are present. Thus, cocamidopropyl betaine may contain variant amounts of other fatty acids found in coconut oil.

An "antimicrobial agent" is a molecule or metal that has the property of stopping or slowing the growth of microbes, e.g. bacteria or fungi. Examples include paraben, methyl isothiazolinone, and diazolidinyl urea.

The term "paraben" refers to alkyl esters of parahydroxybenzoic acid, salts, and combinations thereof, i.e., HO-para-Bz-$CO_2$R, wherein R is alkyl or benzyl or R is a sodium or other metal salt. Parabens have antimicrobial properties. Examples include methylparaben, ethylparaben, propylparaben, butylparaben, heptylparaben, isobutylparaben, and isopropylparaben. The paraben composition may contain a single alkyl or a combination of alkyl groups as esters of parahydroxybenzoic acid. By using a combination of several parabens the effectiveness extends over a broader range of microbes.

The term "*aloe* derived acetylated polymannose" refers to polysaccharide typically obtained by the ethyl alcohol extract of the inner gel of the leaves of an *Aloe* plant such as *Aloe vera, Aloe arborescens, Aloe aristata, Aloe dichotoma, Aloe nyeriensis, Aloe variegate, Aloe barbadensis,* and *Aloe wildii*.

The term "acemannan" refers to the polysaccharide typically obtained by purified ethyl alcohol extract of the inner gel of the leaves of *Aloe barbadensis* Miller. An extract generally comprises about 73% to 90% acemannan. The extract is produced, generally, by removing the outer sheath of the leaf, then removing and processing the inner filet, or mucilage, by pH adjustment, ethanol extraction, freeze drying and grinding. See U.S. Pat. No. 4,735,935. The powder contains a polysaccharide consisting essentially of linear (1-4)-D-mannosyl units. The polysaccharide is a long chain polymer interspersed randomly with acetyl groups linked to the polymer through an oxygen atom. The generic name for the polymer is acemannan. The degree of acetylation is approximately 0.9 acetyl groups per monomer. Neutral sugars linkage analysis indicates that attached to the chain, probably through an alpha(1-6) linkage, is a D-galactopyranose in the ratio of approximately one for every seventy sugars. The 20:1 ratio of mannose to galactose indicates that galactose units are also linked together, primarily by a beta(1-4) glycosidic bond.

A "water absorbent solid material" refers to any variety of materials that absorb water into or on the surface a material but do not entirely dissolve in the water solution. In certain embodiment the water absorbent material is a hydrogel or hydrophilic polyurethane. A contemplated water absorbent material is a one that is sufficiently porous such that capillary action of the pores cause a wicking action of water into the material.

A "hydrogel" refers to any variety of water absorbing polymers which contain carboxyl, hydroxy, or alkoxy containing monomers and forms a gel upon contact with water. Hydrogels may be homopolymeric or copolymeric comprised of two or more different monomer species with at least one hydrophilic component, arranged in a random, block or alternating configuration. Also contemplated are multipolymer interpenetrating polymeric hydrogels made of two independent cross-linked synthetic and/or natural polymer components, contained in a network form or where one component is a cross-linked polymer and other component is a non-cross-linked polymer.

A "hydrophilic polyurethane" or "hydrophilic polyurethane foam" refer to a material made from the polymerization of an isocyanate (e.g., diisocyanates, aromatic, aliphatic, or cycloaliphatic diisocyanates and/or polyisocyanates) and a hydrophilic monomer or polymer. Methods for preparing hydrophilic polyurethanes are reported in U.S. Pat. Nos. 3,861,993, 3,889,417, 4,365,025, 4,384,051, 4,384,051, 7,022,746, 5,650,450, 6,034,149, 8,674,050, 9,364,577, and 9,458,300. Example hydrophilic monomers or polymers include polyesters, polythioethers, polyethers, polycaprolactams, polyepoxides, monomeric dialcohols, for example ethylene glycol, propane-1,2- and -1,3-diol, 2,2-dimethylpropane-1,3-diol, butane-1,4-diol, hexane-1,6-diol, 2-methylpentane-1,5-diol, 2,2,4-trimethylhexane-1,6-diol, 2,4,4-trimethylhexane-1,6-diol, heptane-1, 7-diol, dodecane-1,12-diol, octadec-9,10-ene-1,12-diol, thiodiglycol, octadecane-1,18-diol, 2,4-dimethyl-2-propylheptane-1,3-diol, diethylene glycol, triethylene glycol, tetraethylene glycol, trans- and cis-1,4-cyclohexanedimethanol, ethylene glycol, propylene 1,2- and 1,3-glycol, butylene 1,4- and 2,3-glycol, di-beta-hydroxyethyl butanediol, 1,6-hexanediol, 1,8-octanediol, neopentyl glycol, cyclohexanediol, bis(1,4-hydroxymethyl)propane, 2-methyl-1,3-propanediol, 2-methylpentane-1,5-diol, 2,2,4(2,4,4)-trimethylhexane-1,6-diol, glycerol, trimethylolpropane, trimethylolethane, hexane-1,2,6-triol, butane-1,2,4-triol, tris (beta-hydroxyethyl)isocyanurate, pentaerythritol, mannitol and sorbitol, and also diethylene glycol, triethylene glycol, tetraethylene glycol, dipropylene glycol, polypropylene glycol, polybutylene glycol, xylylene glycol and neopentyl glycol hydroxypivalate, or combinations thereof. Hydrophilic monomers or polymers may be derivatized with isocyanates. Typical isocyanates are diphenylmethylene diisocyanate (MDI), toluidine diisocyanate (TDI) and tetramethylxylylene diisocyanate (TMXDI), isophorone diisocyanate (IPDI), hexamethylene diisocyanate (HDI), dicyclohexylmethane 2,2'-diisocyanate/dicyclohexylmethane 2,4'-diisocyanate/dicyclohexylmethane 4,4'-diisocyanate ($H_{12}$MDI), 2-methylpentane diisocyanate (MPDI), 2,2, 4-trimethylhexamethylene diisocyanate/2,4,4-trimethylhexamethylene diisocyanate (TMDI), norbornane diisocyanate (NBDI).

Ostomy Device

In certain embodiments, this discloser contemplates an ostomy device comprising a deodorizing composition disclosed herein. An "ostomy device" refers to any type of device configured to collect discharge from a stoma that would typically be excreted through the excretory or urinary system. The stoma can be the result of a colostomy, ileostomy, or urostomy. In certain embodiments, the disclosure relates to ostomy devices, for example, an ostomy bag or pouch, configured to collect effluent (e.g., any bodily waste, such as, blood, feces, urine, drainage, etc.) comprising deodorizing compositions disclosed herein. In certain embodiments, the disclosure contemplates deodorizing attachment devices comprising deodorizing compositions disclosed herein. In certain embodiments, the deodorizing attachment devices are used to secure a water absorbent material containing deodorizing compositions disclosed herein inside an ostomy device.

According to embodiments, the devices are configured to neutralize the odors emitted from the container, for example, by retaining and slowly diffusing a deodorizer composition or fluid over the period of wear of the container and thereby may enhance the user's quality of life, particularly in public places. In certain embodiments, the devices are configured so that odor would not escape the pouch each time it is emptied nor require immediate reinsertion of deodorizers into the container to mask odors emitted upon subsequent emptying the pouch. In certain embodiments, the devices and containers according to embodiments thus can eliminate the need for a user to carry deodorizers upon his or her person at all times in an effort to minimize discomfort and embarrassment associated with emitted odors.

FIG. 1 illustrates an embodiment of a container configured to collect effluent. FIG. 1 shows an embodiment of an ostomy pouch (or bag) 10. However, it will be understood that the container may be any container configured to collect effluent, including but not limited to, a fistula pouch, a fecal or urinary bedside drainage bag or any other device or container in which feces, urine, or any malodorous material can be collected.

The ostomy pouch 10 may be any type of ostomy pouch and is not limited to the construction shown in the FIG. 1. The ostomy pouch 10 may be an open ended pouch, closed ended pouch, a one-piece system, a two-piece system, or some combination thereof.

In some embodiments, the ostomy pouch 10 may include a first surface 12 (also referred to as an "interior" or "inside opening"). In some embodiments, the pouch 10 may include a first opening 13 (also referred to as "entrance opening"), for example, for a closed ended pouch. In the ostomy pouch 10 may further include a second opening 14 (also referred to as a "tail opening"), for example, for an open ended pouch.

In some embodiments, the ostomy pouch 10 may include a deodorizing device 30. The device 30 may be configured to neutralize odors associated with the effluent by deodorizing and/or reducing (or suppress) bacterial growth. The device 30 may be configured to contact the effluent (e.g., bodily waste) and disperse a deodorizing composition or fluid into the effluent.

In some embodiments, the deodorizing device 30 may include a carrier platform (also referred to as a "carrier") 16. The carrier 16 may include water absorbent material such as a hydrogel or hydrophilic polyurethane foam comprising a deodorant composition or fluid disclosed herein and/or optionally additional silver ions and/or antimicrobial features. The silver, preferably in the form of a silver compound, and/or the anti-bacterial compounds, may be configured to inhibit or reduce bacterial growth, thereby reducing the odorous gases generated by the bacteria in the effluent.

In some embodiments, the carrier 16 may include a base substrate 15, for example, as shown in FIG. 2C. The base substrate 15 may be an absorbent material configured for two-way fluid flow. The base substrate 15 may be configured to retain, as well as disperse, fluid or deodorizing composition disclosed herein. For example, the base substrate 15 may be filled with a deodorizer fluid, configured to retain a deodorizer fluid and disperse the deodorizer fluid into the effluent when the base substrate 15 absorbs the effluent. In some embodiments, the base substrate 15 may have properties similar to hydrophilic polyurethane foam absorbent pad with a deodorizing composition disclosed herein and optionally containing antimicrobial agent.

In some embodiments, the carrier 16 may optionally include a surface layer 17, as shown in FIG. 2C. The surface layer 17 may be a moisture vapor permeable film. The layer 17 may have antimicrobial properties and/or be configured for surface wicking.

In some embodiments, the device 30 may include a mesh or porous film 18 that at least partially envelopes or surrounds the carrier 16. The film 18 may include openings configured to allow the deodorizing composition or fluid to move from the carrier 16 into the effluent (not shown).

In some embodiments, the device 30 may be integrated and/or fixedly (or permanently) fastened to the ostomy pouch 10. In some embodiments, the device 30 may be permanently bonded to an ostomy pouch. In some embodiments, the mesh or vented film 18 may be configured to hold the carrier 16 in place with respect to the ostomy pouch 10. The mesh or vented film 18 may be glued, welded, heat sealed, or bonded by some other convenient technique, to the inside surface 12 of ostomy pouch 10 at several different points, only two of which, 20A, 20B, are shown for clarity of illustration. The mesh or vented film 18 may only need be glued or welded to the ostomy pouch at a sufficient number of points and with sufficient bonding to hold the carrier 16 in the ostomy pouch for the expected duration of use of the pouch. In some embodiments, the device 30 may be configured to be disposed close to the bottom, for example, about 2 inches above the bottom (e.g., second opening 14) of the pouch 10.

In other embodiments, the deodorizing device 30 may be configured to be attached to an ostomy pouch. The deodorizing device 30 may further include a fastener 21 to attach the device 30 to an ostomy pouch. The fastener 21 may include but is not limited to an adhesive. In some embodiments, the fastener 21 may be configured to provide sufficient bonding to hold the carrier 16 in the ostomy pouch for the expected duration of use of the pouch. The consumer can then use a new carrier with a clean pouch with each pouch change. In other embodiments, the fastener 21 may be configured to remove the deodorizing device 30 from a pouch without damaging the pouch so as to allow the device deodorizing 30 to be replaced in situations, for example, where replacement of the entire ostomy pouch 10 is not convenient. Thus, the device can be readily removed and replaced with a fresh carrier.

In some embodiments, the fastener 21 may be disposed on a surface 24 of the deodorizing device 30. The surface 24 may be integrated and/or attached to the mesh vented film 18 so that the carrier 16 is completely enveloped or surrounded. In some embodiments, the fastener 21 may be protected with a protective layer 22. As shown in FIG. 2A, the device 30 may include the carrier 16, enclosed by a mesh or vented film 18 and the surface 24, with fastener 21 disposed on the surface 24, and the protective layer 22 covering the fastener 21. The protective layer 22 can be configured to be removed, such as by peeling it off, to expose the fastener 21. The carrier 16 with the mesh or vented film 18 can then be inserted inside an ostomy pouch, such as the pouch 10, and pressed so that the exposed fastener 21 contacts and sticks to the inner surface 12.

The film 18 may be disposed above one or more surfaces of the carrier 16. In some embodiments, the film 18 may fully surround or envelope the carrier 18. In other embodiments, the carrier 16 may be at least partially surround or envelope the carrier 18. In some embodiments, the film 18 may be disposed above the top surface (also referred to as "first surface"; e.g., the surface perpendicular to the opening 13), the opposing side surfaces (also referred to as the "second and third surfaces"; e.g., the surfaces parallel to the opening 13), or some combination thereof.

Figure 3A:
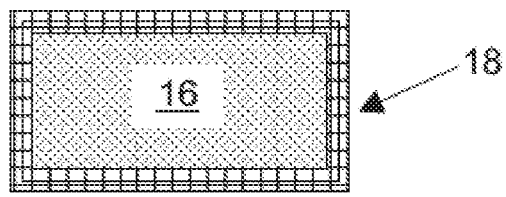
FIG. 3A illustrate embodiments of a deodorizing device disclosed herein.
Figure 3B:
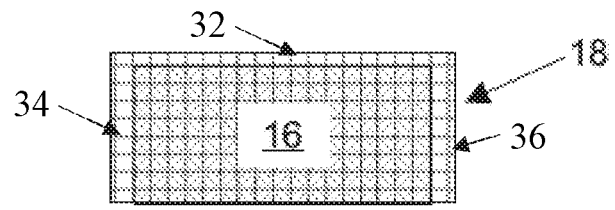
FIG. 3B illustrate embodiments of a deodorizing device disclosed herein.

FIGS. 3A and 3B illustrate an end view and a side view, respectively, of the device 30 according to certain embodiments, FIGS. 3A and 3B illustrate the device 30 in which the film 18 partially envelopes the carrier 16 by being disposed above surfaces 32, 34, and 36 of the carrier 16. This allows the deodorizing fluid 26 to more easily reach and be absorbed by the carrier 16, rather than having to go through the mesh or film 18 to be absorbed by the carrier 16.

In other embodiments, the deodorizing device 30 may omit the film 18. FIG. 2B illustrates the deodorizing device 30 without a mesh or vented film 18 including the fastener 21 covered by the protective layer 22.

Figure 4:
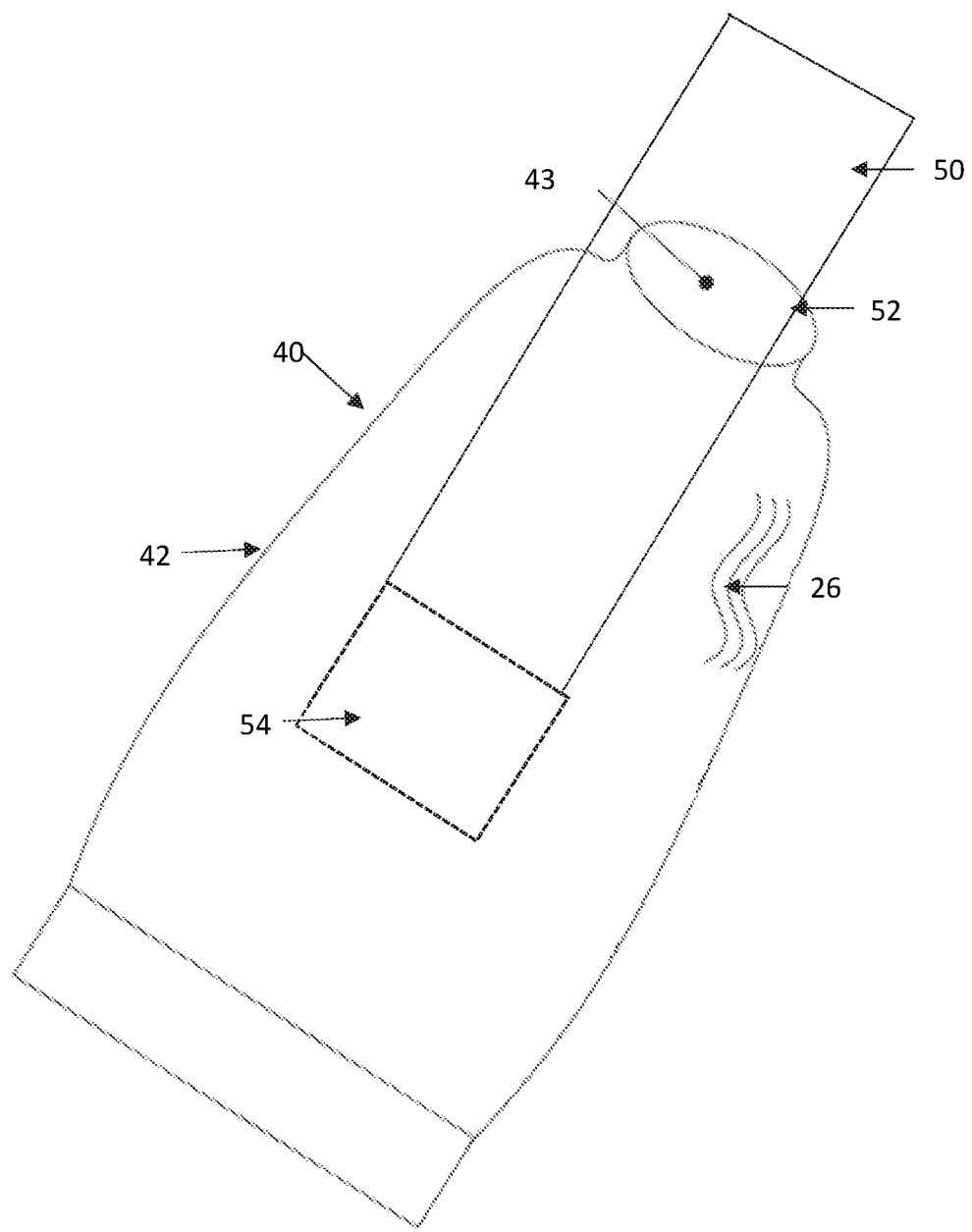
FIG. 4 illustrates embodiments of an ostomy pouch.

In some embodiments, for example, an ostomy pouch may include a pocket for the device 30. The pocket may include at least a section that may be similar to film 18 and may be configured to fixedly hold the device 30, for example, close to the bottom (e.g., about 2 inches above the bottom of the pouch). FIG. 4 illustrates an example of a container (e.g., ostomy pouch) 40, having a pocket 50 configured to receive a deodorizer device 30. In some embodiments, the ostomy pouch 40 may include a first surface 42 (also referred to as an "interior" or "inside surface") and at least one opening 43. In some embodiments, the pocket 50 may be disposed on one side of the surface 42. In other embodiments, the pocket 50 may be disposed on an outside surface of the pouch 40.

In some embodiments, the pocket 50 may include at least one section. In some embodiments, the pocket 50 includes more than one section, for example, two sections. As shown in FIG. 4, the pocket 50 may include a first section 52 and a second section 54. The first section 52 may be disposed above the second section 54 closer to the opening 43. The second section 54 may be configured to at least temporarily, fixedly hold the device 30. In some embodiments, the second section 54 may at least include a mesh film, like film 18, on one side, configured to allow two-way flow between the effluent and device 30. The film may be disposed to contact the effluent. The first section 52 may be made of a solid (no mesh) material. In some embodiments, the first section 52 may be configured to extend past the opening 43 so that when the pouch 40 is clamped or fastened, the pocket 50 is fixedly closed and sealed. In some embodiments, the device 30 may be preloaded with a deodorizing fluid 26. The deodorizing fluid 26 can be any of the compositions disclosed herein.

In some embodiments, for example, if the deodorizing device 30 is preloaded with the deodorizing fluid 26, the deodorizing device 30 may further include a protective layer 28 configured to cover the film 18 to protect the deodorizing device 30 and configured to be removed. The protective layer 28 may be for example, a tab, or other mechanism, that may be configured to be removed by pulling, to thereby allow the deodorizing composition or fluid to exit the deodorizing device 30 into the pouch.

In other embodiments, the deodorizing composition or fluid 26 can be added. In some embodiments, the composition or fluid 26 can be poured or squirted into the pouch 10, or directly onto the carrier 16. The carrier 16 may then absorb the deodorizing composition or fluid 26 and gradually move the deodorizing fluid from the carrier 16 into the effluent. The deodorizing composition or fluid 26 may be introduced via the entrance opening 13 of the pouch and/or the tail opening 14. Once the deodorizing composition or fluid 26 is absorbed by the carrier 16, the carrier 16 is configured to substantially withhold or retain the composition fluid 26, although some leakage may occur, until the level of effluent (not shown) in the pouch reaches the level of the carrier. At this point, the carrier 16 is configured to slowly diffuse or disperse the deodorizing fluid through the mesh or vented film 18 into the effluent in the ostomy pouch 10. The carrier 16 thus may also be configured to reduce the amount of deodorizing liquid that is lost when the pouch is emptied.

Thus, the usable wearing time of an ostomy pouch has been extended, thereby providing a convenience and significant cost savings to the user due to less frequent pouch changes as a result of odor. Also, the amount of deodorizing fluid that must be used has been reduced, thereby providing both a convenience and a cost-savings to the user.

Although the preferred embodiment is for the carrier to be a hydrophilic polyurethane foam comprising a deodorant composition disclosed herein, the carrier may also be an untreated carrier, in which case the deodorizing composition would be applied to the carrier, such as in the form of a liquid. In this case, if desired, the antimicrobial compounds may be included in the deodorizing compositions or liquid disclosed herein 26.

It will be understood that although the deodorizing device 30 has been primarily described for use with an ostomy pouch, the deodorizing device 30 can also be used with a fistula pouch, a fecal or urinary bedside drainage pouch or any other device or container in which feces or urine is collected.

According to some embodiments, the deodorizing device 30 may be single use or be disposable. According to some embodiments, a portion or any combination of the devices, containers or pouches, and/or deodorizing fluids may be sold as a kit.

In some embodiments, the kit may include at least one device, according to embodiments, and deodorizing fluid. In some embodiments, the kit may include a plurality of deodorizing devices and a bottle of deodorizing composition or fluid disclosed herein.

In other embodiments, the kit may include a plurality of deodorizing devices preloaded with a deodorizing fluid. In further embodiments, the kit may also include a bottle of a deodorizing fluid.

In some embodiments, the kit may include at least one ostomy pouch or other kind of drainage pouches, containers or devices. In some embodiments, the pouch may include the deodorizing device. In other embodiments, the kit may include at least one deodorizing devices. In further embodiments, the kit may include a plurality of pouches and devices, optionally preloaded with a deodorizing fluid. The kit may also include a bottle of deodorizing fluid.

In some embodiments, the kit may include a port configured to infuse the deodorizer fluid into the effluent.

In some embodiments, the kit comprises an ostomy device disclosed herein, a deodorizing composition disclosed herein, and optionally, and optionally a water absorbent material disclosed herein.

Examples

A deodorizing solution designed for eliminating unpleasant odors from bodily excretions collected in ostomy pouches or other containers Several liquid deodorizers for ostomy pouches have been investigated. Citric acid, sodium citrate, and coco betaine mixes well with no issues. Zinc ricinoleate and copper chlorophyllin complex were identified as potential deodorants. Other optional additives contemplated are cyclodextrans, amphiphilic polymers, e.g., polyethylenimine (PEI), and antimicrobial metallic salts—silver, gold, zinc, copper.

Steps for making the master batch deodorant solution: make the salt solution with 15 g of citrate (1.5 teaspoons), 5 g of citric acid (0.5 teaspoons), and 20 grams (=20 ml of water) of water. Add 10 ml of coco betaine slowly 10 ml of Deoconcentrate (zinc ricinoleate). Slowly add the salt solution to the coco/deo solution and mix well. CocoBetanine is 30% solids. DeoConcentrate is 40% solids, i.e., 20% is zinc ricinoleate, 13% is tetrahydroxy propyl ethyenediamine, and 7% sodium lauroyl sarcosinate.

The master batch can be diluted with additional water to vary the concentration of the actives.

Further optimization resulted in a deodorizing composition according to Table 1.

TABLE 1

DEODORIZING SOLUTIONS WITH PRESERVATIVES

| Ingredient | Weight (grams) | % of total | Mixing |
| --- | --- | --- | --- |
| Sodium Citrate | 15 | 5.5% | Solution 1 |
| Citric Acid | 5 | 1.8% | |
| Purified boiling hot water | 20 | 7.4% | |
| Coco Betaine | 12.5 | 4.6% | Solution 2 |
| DeoConcentrate | 12.5 | 4.6% | |
| zinc ricinoleate | | | |
| tetrahydroxy propyl ethylenediamine | | | |
| sodium lauroyl sarcosinate | | | |
| Water from cocobetaine and deoConc | | | |
| Purified boiling hot water | 200 | 73.8% | Solution 3 |
| Paraben DU | 5 | 1.8% | |
| Paraben DU Actives | | | |
| propylene glycol in DU (solvent) | | | |
| Acemannan Hydrogel | 1 | 0.4% | |
| Total | 271 | 100.0% | |

Composition for impregnating an extended wear carrier with an added preservative is provided in Table 2.

TABLE 2

IMPREGNATION SOLUTION

| Ingredient | Weight (grams) | % of total |
| --- | --- | --- |
| Sodium Citrate | 15 | 24.0% |
| Citric Acid | 5 | 8.0% |
| Water | 20 | 32.0% |

TABLE 2-continued

IMPREGNATION SOLUTION

| Ingredient | Weight (grams) | % of total |
|---|---|---|
| Coco Betaine | 10 | 16.0% |
| DeoConcentrate | 10 | 16.0% |
| zinc ricinoleate | | |
| tetrahydroxy propyl ethylenediamine | | |
| sodium lauroyl sarcosinate | | |
| Water from cocobetaine and deoConc | | |
| Paraben | 2.5 | 4.0% |
| Total | 62.5 | 100.0% |

Add Acemannan hydrogel to impregnation solution 0.25 g to 0.50 g.

Impregnated Extended Wear Carrier for Liquid Deodorizers in an Ostomy Pouch and Containment Devices A deodorizing carrier pad has been designed to be placed inside an ostomy pouch for odor control containing a hydrophilic polyurethane foam. The hydrophilic polyurethane foam is impregnated with a deodorizing salt mixture. The carrier optionally contains a water permeable or impermeable film (plastic) with an adhesive or glue which allows for placement of the carrier inside a desire area of the ostomy pouch. The adhesive prevents movement of the carrier after affixing the carrier inside an ostomy pouch. The carrier may have a tail like attachment (tail) in the form of plastic strip or similar attachment of approximately 2" to 3" in length. The tail extends through the stoma opening of the pouch to the exterior of the pouch, where it is then attached to the adhesive barrier of the pouch, or it is secured by a separate flange that is attached to the pouch. The attachment can also be secured by another adhesive, barrier ring, paste and/or another type of ostomy accessory. By using a tail attachment, the carrier can be either suspended within the pouch by the tail, or attached to the interior wall of the pouch with an adhesive.

Citric acid and sodium citrate provided a noticeable difference in odor control; however, but the foam was too stiff with the combination alone. The best combination of products were citric acid, sodium citrate, coco betaine and zinc ricinoleate. The hydrophilic polyurethane carrier impregnated with the combined solution was soft and effective. The deodorant solution can be added to the carrier as needed.

Hydrophilic Polyurethane Foam—density is 91.4 kg/m$^3$ (nominal) so the weight of the foam is calculated to be 5.9 grams (1 inch×1 inch×0.25 inch foam). At a 10× absorption (weight based) the foam sample would absorb 59 grams of the solution for a total weight of 64.9 g. If all of the water evaporated that would leave the following in the foam: 15 g of citrate, 5 g of citric acid, 3 grams of coco betaine, 2 grams of zinc ricineolate, 1.3 grams of tetrahydroxy propyl ethylenediamine, 0.7 grams of sodium lauroyl sarcosinate. Provided is the percent by weight after adding the aqueous deodorant to the hydrophilic polyurethane foam: 15 g of citrate (23.1%), 5 g of citric acid (7.7%), 3 grams of coco betaine (4.6%), 2 grams of zinc ricineolate (3.1%), 1.3 grams of tetrahydroxy propyl ethylenediamine (2.0%), 0.7 grams of sodium lauroyl sarcosinate. An adhesive or glue could be used to secure the polyurethane foam to an ostomy pouch.

The invention claimed is:

1. A deodorizer composition for deodorizing an ostomy device comprising:
   (a) a combination of citric acid and a citric acid salt;
   (b) cocamidopropyl betaine;
   (c) zinc ricinoleate;
   (d) acemannan; and
   (e) an aloe derived acetylated polymannose.

2. An ostomy pouch comprising a deodorizer composition for deodorizing an ostomy device, the deodorizer comprising:
   (a) a combination of citric acid and a citric acid salt;
   (b) cocamidopropyl betaine;
   (c) zinc ricinoleate;
   (d) acemannan; and
   (e) an aloe derived acetylated polymannose.

* * * * *